United States Patent

Eckhouse et al.

Patent Number: 5,833,612
Date of Patent: Nov. 10, 1998

[54] METHOD AND APPARATUS FOR DIAGNOSIS SKIN LESIONS

[75] Inventors: Shimon Eckhouse; Michael Kreindel, both of Haifa, Israel

[73] Assignee: ESC Medical Systems, Ltd., Yokneam, Israel

[21] Appl. No.: 594,891

[22] Filed: Feb. 9, 1996

[51] Int. Cl.$^6$ .................................................. A61B 5/00
[52] U.S. Cl. ...................................... 600/476; 250/461.2
[58] Field of Search ..................................... 128/633, 665, 128/664; 604/20; 606/9, 3, 10; 356/319, 448; 250/330, 574, 358.1, 461.2

[56] References Cited

U.S. PATENT DOCUMENTS

| | | | |
|---|---|---|---|
| 4,515,165 | 5/1985 | Carroll | 128/664 |
| 4,555,179 | 11/1985 | Langerholc et al. | |
| 4,894,547 | 1/1990 | Leffell et al. | 250/461.2 |
| 5,146,923 | 9/1992 | Dhawan | |
| 5,363,854 | 11/1994 | Martens et al. | 128/665 |

FOREIGN PATENT DOCUMENTS 4031320A of 0000 Germany.

OTHER PUBLICATIONS

S. L. Jacques, Role of Skin Optics in Diagnostic and Therapeutic Uses of Lasers, Laser in Dermatology, Springer–Verlag, 1991, pp. 1–21.

*Primary Examiner*—George Manuel
*Assistant Examiner*—Eleni Mantis Mercader
*Attorney, Agent, or Firm*—Cobrin Gittes & Samuel

[57] ABSTRACT

A method and apparatus for determining skin lesion parameters comprise directing light to the skin in which the lesion is located and monitoring the reflection of that light. Then, the spatial and spectral distribution of the reflected light is analyzed. The depth is determined by finding a location where the difference between a spectral intensity of reflected light and an average reflected intensity is greater than a maximal difference between the intensity of each point and an average intensity for normal skin. The wavelength of the light reflected from the location is determined, and from the wavelength the penetration depth is determined. The penetration depth is also the depth of the lesion below the skin surface. The size is determined by determining a plurality of locations where the deviation between the spectral intensity and the average intensity is greater than the maximal deviation for normal skin. Based on the spatial distribution of the locations the size of the lesion is determined.

7 Claims, 1 Drawing Sheet

5,833,612

METHOD AND APPARATUS FOR DIAGNOSIS SKIN LESIONS

FIELD OF THE INVENTION

The present invention relates generally to the art of diagnosing skin lesions. More particularly, the invention relates to a method and apparatus for analyzing the spatial and spectral distribution of light reflected by a skin lesion to diagnose the lesion, for example, by determining skin type, lesion size and depth.

Skin lesions may be treated a number of ways. One known treatment method includes directing laser and/or noncoherent pulsed light. The lesion absorbs energy from the light and is thus treated (by coagulation e.g.). This method is particularly useful for treating vascular, pigmented and malignant lesions. Generally, such a treatment is based on selective thermocoagulation of vessels or protein. One possible side effect of such treatment, if done improperly, is damage of the surrounding tissue by the light energy.

Effective treatment of a skin lesion without damaging the surrounding tissue is easier if light pulse parameters, such as pulse duration, spectrum, pulse energy, spot size and delay between consequent pulses, are properly selected. Proper selection of the optimal parameters for an individual patient depends on knowledge of the lesion location depth and diameter, as well as the patient's skin type or pigmentation level. See, for example, S. L. Jacques, Role of Skin Optics in Diagnostic and Therapeutic Uses of Lasers, *Laser in Dermatology,* Springer-Verlag, 1991, pp. 1–21. Knowledge of these parameters contributes significantly to the success of photothermolysis treatment of various problems such as vascular, pigmented and malignant lesion.

Thus, there is a need to diagnose the patient's skin pigmentation, the lesion depth and the lesion size. Ultrasound diagnostics can be used for determination of lesion size and location but it does not give information about skin pigmentation. Consequently a method and apparatus for diagnosing all of these clinical parameters is desirable.

Moreover, such a method should be effective, and relatively easy to use. Additionally, such a method should be useful for follow-up diagnostics of lesion transformation, and take into account any changes in skin color.

SUMMARY OF THE PRESENT INVENTION

In accordance with one aspect of the invention a method and apparatus for determining skin lesion parameters comprise directing light to the skin in which the lesion is located and monitoring the reflection of that light. Then, the spatial and spectral distribution of the reflected light is analyzed.

In one embodiment the lesion depth and lesion size are determined, and the skin type or pigmentation is determined. In another embodiment the depth and size are determined by determining a maximal deviation in the reflected spectrum digitally.

The reflected light may be monitored by scanning with a small spot size spectrum analyzer or using an array of sensors for full area monitoring.

In one embodiment the analysis includes determining a spatial and spectral distribution of the reflected light and calculating an average reflected spectrum and a reflected spectrum deviation from the average spectrum. The deviation of the spectrum reflected by the lesion is compared to a deviation of a spectrum reflected by normal skin and a numerical analysis of the relative differences in the reflected spectra is used to determine the location and size of the lesion.

In another embodiment the analysis includes calculating an average reflected spectrum of normal skin, in accordance with the formula $$J_s(\lambda) = \frac{[\Sigma J_x(\lambda)]}{n}$$

where $J(\lambda)$ is a reflected light spectral intensity for point n and $\lambda$ is wavelength. Then a maximal difference between the average reflected spectrum, $J_s(\lambda)$, and each individual point, $J_x(\lambda)$ is calculated. The average spectral intensity of reflected light is compared with a standard reflection spectra for the skin to determine the type of skin being diagnosed.

In yet another embodiment the analysis includes determining the depth of the lesion by finding a location where the difference between a spectral intensity of reflected light and an average reflected intensity is greater than a maximal difference between the intensity of each point and an average intensity for normal skin. The wavelength of the light reflected from the location is determined, and from the wavelength the penetration depth is determined. The penetration depth is also the depth of the lesion below the skin surface.

In yet another embodiment the analysis includes determining the size of the lesion by determining a plurality of locations where the deviation between the spectral intensity and the average intensity is greater than the maximal deviation for normal skin. Based on the spatial distribution of the plurality of locations the size of the lesion is determined.

Other principal features and advantages of the invention will become apparent to those skilled in the art upon review of the following drawings, the detailed description and the appended claims.

BRIEF DESCRIPTION OF THE DRAWINGS

For a better understanding of the invention, reference is made to the accompanying drawings, in which like numerals designate corresponding elements or sections throughout, and in which.

Figure 1:
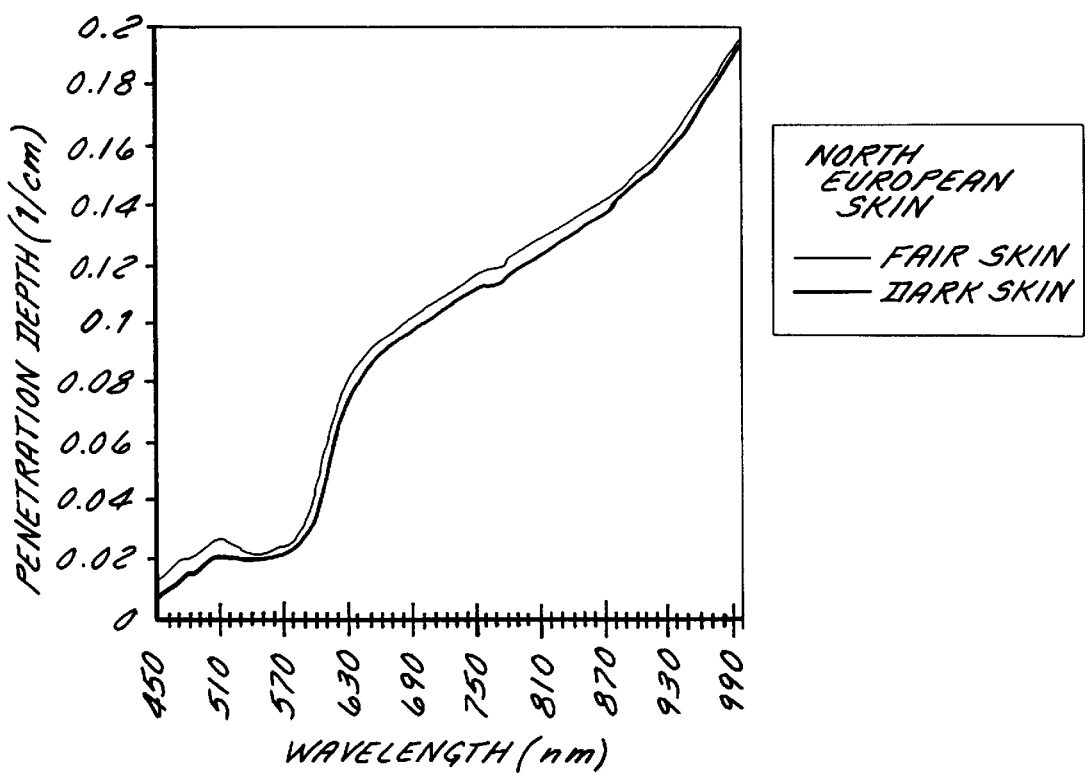
FIG. 1 is a graph showing effective penetration depth of light into the bloodless skin (dermis) as a function of wavelength in the range of 400 nm to 1000 nm for the different case of skin pigmentation.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

The invention relates to a new method and apparatus for diagnosing skin lesions. More particularly the invention provides for determining the location and size of a skin lesion, as well as a patient's skin pigmentation (type). The invention will also allow for follow-up diagnosis, taking into account changes in skin pigmentation.

Generally, in accordance with the present invention, a spectral and spatial analysis of reflected visible light is used to determine the full set of clinical parameters such as skin pigmentation, lesion size and depth. A lesion image is analyzed using the dependence of light penetration into tissue on wavelength, and differences between the optical properties of normal skin and lesions. Specifically, an analysis of the spatial distribution of color balance, determining the reflected spectrum of normal skin, and comparing that to the reflected spectrum of lesion allows determination of lesion location and size.

Additionally, using standard illumination of skin surface, skin pigmentation and peculiarities of light interaction with skin can be determined.

The effective depth that light penetrates into the skin can be estimated by using the effective attenuation coefficient of the dermis ($\mu_{eff}$) that takes into account scattering and absorption of light. Following Jacques (above) the effective attenuation coefficient of the skin can be written as:

$$\mu_{eff} = 3\mu_a[\mu_a + \mu_s(1-g)]^{1/2}$$

where $\mu_a$ is the absorption coefficient of dermis, $\mu_s$ is the scattering coefficient of dermis, g is the anisotropy factor, which is defined as the average cosine of scattering angle for one scattering event.

Given the effective attenuation coefficient, $\mu_{eff}$, the effective penetration depth (d) can be estimated from $d=1/\mu_{eff}$. The effective penetration depth, d, is shown in FIG. 1 for fair and dark northern European skins as a function of wavelength.

The effective penetration depth -d is defined as the depth at which the fluence of the light in the skin is 1/e of the value of the fluence of the light that impinges on the surface of the skin. As may be seen on the graph, penetration is nearly four times greater when the wavelength is 650 nm, compared to 400 nm. Penetration depths of 1 mm (0.1 cm) can be achieved at a red light (560–660 nm), penetration depths of 0.7 mm are achieved by green light, and blue light does not penetrate beyond depths as little as 0.45 mm. As shown on the graph, radiation with longer wavelengths penetrates more deeply into the skin.

One important feature of lesions is that they cause changes in reflected light color. The present invention utilizes that feature and the varying penetration of light by analyzing the changes in reflected light color to determine the depth of the lesion. The wavelength of the changed color is responsive to the depth of the lesion. For example, changes in the red part of spectrum occur if the lesion is located at a depth of more than 0.7 mm.

Moreover, the changes in reflected light color can also be used to determine lesion size. Specifically, lesion size is determined by an analysis of the spatial distribution of the spectrum changes caused by the lesion.

According to one embodiment of the present invention the spatial and spectral reflection image of the skin surface can be realized by area scanning with a small spot size spectrum analyzer. In accordance with a second embodiment of the invention the spatial and spectral reflection is realized by full area analysis with a spectral sensitive array of sensors.

Figure 2:
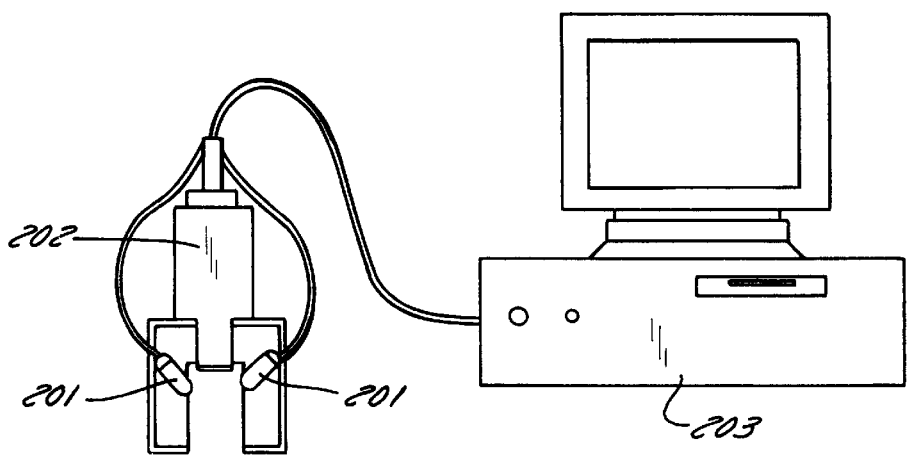
FIG. 2 is a block diagram of the device for spectral and spatial analysis of the reflected light.

The device used to implement one preferred embodiment of the invention is shown in FIG. 2 and includes a light source 201, a spectrum analyzer 202, and a computer 203.

Light source 201 is preferably calibrated and is used to illuminate the surface of the skin. Moreover, the light source is preferably capable of providing light over a range of wavelengths. One suitable light source would be a flashlamp. Filters may be used to remove unwanted wavelengths.

Spectrum analyzer 202 includes something to monitor the light, such as a CCD camera connected to computer 203 through an imaging processing board which is part of computer 203. In a preferred embodiment the CDD camera is a color CCD camera and it is used as a simple spatial and three color spectrum analyzer. In addition to an imaging processing board computer 203 includes software for spatial and spectral distribution light reflection analysis. Computer 203 is used because of the ability to process data, however, the data may be processed with other means, such as analog circuitry, or manually.

Using the apparatus described above (or other suitable apparatus) the analysis of skin lesions includes the following steps: reading the spatial and spectral distribution of the reflected light; calculating the average reflected spectrum of normal skin and the deviation of the spectrum reflected by normal skin from the average spectrum reflected by normal skin; determining the type of skin; comparing the spectrum reflected by the lesion to the average spectrum reflected by normal skin of that type; performing a numerical analysis of the relative changes in the reflected spectrum; and determining the depth and size of the lesion from the data.

One suitable manner in which the analysis of the reflected light spectrum of normal skin follows. To calculate average reflected spectrum of normal skin, the reflected light spectral intensity, $J(\lambda)$, at n points is measured. Given the measured $J(\lambda)$ for each point n, the average reflected light spectral intensity is given by:

$$J_s(\lambda) = \frac{[\Sigma J_x(\lambda)]}{n}$$

where $\lambda$ is wavelength.

A maximal difference, $\Delta J(\lambda)$, between $J_s(\lambda)$ and $J_x(\lambda)$ gives the spectral variation of normal skin reflection. The skin pigmentation is determined by comparing the average spectral intensity of reflected light with the standard reflection spectra for different skin types.

The lesion depth is determined by finding the location where the difference between the spectral intensity of the light reflected by the lesion and $J_s(\lambda)$ is greater than $\Delta J(\lambda)$ (i.e., the deviation is larger than normal). Then the maximal wavelength, $\lambda_{max}$, at the locations having larger than normal deviations between the lesion reflection and $\Delta J(\lambda)$ occurs is determined. Finally, using $\lambda_{max}$ and the graph of FIG. 1, the penetration depth is determined. The penetration depth gives the distance, $1(x,y)$, from the skin surface to the lesion. Thus, the lesion depth is determined. Analysis of spatial distribution of $1(x,y)$ gives the lesion size.

Thus, it should be apparent that there has been provided in accordance with the present invention a method and device for diagnosing skin lesions that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of determining skin lesion parameters comprising the steps of:

directing light to the skin in which the lesion is located;

monitoring light that is reflected; and analyzing the spatial and spectral distribution of the reflected light, wherein the step of analyzing includes the steps of:

calculating an average reflected spectrum of normal skin, in accordance with the formula $$J_s(\lambda) = \frac{[\Sigma J_x(\lambda)]}{n}$$

where $J(\lambda)$ is a reflected light spectral intensity for point n and $\lambda$ is wavelength;

calculating a maximal difference between the average reflected spectrum, $J_s(\lambda)$, and each individual point $J_x(\lambda)$; and comparing an average spectral intensity of reflected light with a standard reflection spectra for the skin.

2. A method of determining skin lesion parameters comprising the steps of:

directing light to the skin area in which the lesion is located;

simultaneously monitoring light that is reflected at a plurality of individual spectra;

determining a location where a difference between a spectral density of reflected light and an average reflected intensity of the reflected light is greater than a maximal difference between the intensity of each point and an average intensity for normal skin;

determining wavelength of the light reflected from the location; and determining the penetration depth of the reflected light, wherein the depth of the lesion from the skin surface is determined to be the penetration depth.

3. A method of determining skin lesion parameters comprising the steps of:

directing light to the skin in which the lesion is located;

monitoring light that is reflected; and analyzing the spatial and spectral distribution of the reflected light, wherein the step of analyzing includes the step of determining the depth of the lesion by:

determining a location where a difference between a spectral intensity of reflected light and an average reflected intensity is greater than a maximal difference between the intensity of each point and an average intensity for normal skin;

determining wavelength of the light reflected from the location; and determining the penetration depth of the reflected light, wherein the depth of the lesion from the skin surface is determined to be the penetration depth; and includes the step of determining the size of the lesion by:

determining a plurality of locations where the difference between the spectral intensity and $J_s(\lambda)$ is greater than $\Delta J(\lambda)$;

analyzing the spatial distribution of the locations; and determining the size of the lesion from the spatial distribution.

4. An apparatus of determining skin lesion parameters comprising;

a source of light disposed in a housing and capable of directing the light to the surface of the skin;

a monitor disposed to receive light reflected by the skin simultaneously at a plurality of individual spectra; and means for analyzing a spatial and spectral distribution of the reflected light;

means for calculating an average reflected spectrum;

means for calculating a reflected spectrum deviation from the average spectrum;

means for comparing the deviation to a deviation of light reflected from normal skin and generating relative differences in the reflected spectra;

means for performing a numerical analysis of the relative differences in the reflected spectra; and means for determining the location and size of the lesion from the numerical analysis.

5. An apparatus for determining skin lesion parameters comprising:

a source of light, disposed in a housing and capable of directing the light to the surface of the skin;

a monitor disposed to receive light reflected by the skin; and means for analyzing the spatial and spectral distribution of the reflected light, wherein means for analyzing includes means for calculating an average reflected spectrum of normal skin, in accordance with the formula $$J_s(\lambda) = \frac{[\Sigma J_x(\lambda)]}{n}$$

where $J(\lambda)$ is a reflected light spectral intensity for point n and $\lambda$ is wavelength;

means for calculating a maximal difference between the average reflected spectrum, $J_s(\lambda)$, and each individual point $J_x(\lambda)$; and means for comparing an average spectral intensity of reflected light with a standard reflection spectra for the skin.

6. An apparatus for determining skin lesion parameters comprising:

a source of light, disposed in a housing and capable of directing the light to the surface of the skin;

a monitor disposed to receive light reflected by the skin;

means for analyzing the spatial and spectral distribution of the reflected light;

means for determining a location where a difference between the spectral intensity of the reflected light and an average reflected intensity of the reflected light is greater than the maximal difference between the intensity of each point and an average intensity for normal skin;

means for determining wavelength of the light reflected from the location; and means for determining the penetration depth, of the reflected light, and wherein the depth of the lesion from the skin surface is determined to be the penetration depth.

7. An apparatus for determining skin lesion parameters comprising:

a source of light, disposed in a housing and capable of directing light to the surface of the skin;

a monitor disposed to receive light reflected by the skin; and means for analyzing the spatial and spectral distribution of the reflected light, wherein the means for analyzing includes;

means for determining a location where a difference between a spectral intensity of reflected light and an average reflected intensity is greater than a maximal difference between the intensity of each point and an average intensity for normal skin;

means for determining wavelength of the light reflected from the location;

means for determining the penetration depth of the reflected light, wherein the depth of the lesion from the skin surface is determined to be the penetration depth;

means for determining a plurality of locations where the difference between the spectral intensity and $J_s(\lambda)$ is greater than $\Delta J(\lambda)$;

means for analyzing the spatial distribution of the locations; and means for determining the size of the lesion from the spatial distribution.

* * * * *